(12) United States Patent
Gledhill et al.

(10) Patent No.: US 6,245,524 B1
(45) Date of Patent: *Jun. 12, 2001

(54) PHENYLACETYL-COA LIGASE FROM PENICILLIUM CHRYSOGENUM

(75) Inventors: Linden Gledhill, King of Prussia, PA (US); Philip Andrew Greaves; John Patrick Griffin, both of Worthing (GB)

(73) Assignee: SmithKline Beecham p.l.c., Brentford (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 21 days.

(21) Appl. No.: 08/981,215
(22) PCT Filed: Jun. 26, 1996
(86) PCT No.: PCT/EP96/02799
  § 371 Date: Feb. 11, 1998
  § 102(e) Date: Feb. 11, 1998
(87) PCT Pub. No.: WO97/02349
  PCT Pub. Date: Jan. 23, 1997

(30) Foreign Application Priority Data

Jun. 30, 1995 (GB) .................................................. 9513403

(51) Int. Cl.[7] .............................. C07K 21/06; C12N 9/00; C07H 17/00
(52) U.S. Cl. .................. 435/69.1; 435/183; 435/325; 435/320.1; 536/23.2; 536/23.1
(58) Field of Search .................................. 435/69.1, 183, 435/325, 320.1; 536/23.2, 23.1

(56) References Cited

FOREIGN PATENT DOCUMENTS

WO 96/10085    4/1996  (WO) ............................ C12N/15/52

OTHER PUBLICATIONS

Grunert et al. Archives of Biochemistry 30:217–225, 1951.*
Kogekar, et al., "Biosynthesis of Penicillin in vitro: Purification & Properties of 'Phenyl/Phenoxyacetic Acid Activating Enzyme", *Indian Journal of Biochemistry & Biophysics*, 19: 257–261 (1982).
Martinez–Blanco, et al., "Isolation and Characterization of the Acetyl–CoA Synthetase from *Penicillium chrysogenum*", (1992), Journal of Biological Chemistry, vol. 267, No. 8, pp. 5474–5481.
Martinez–Blanco, et al., "Purification and Biochemical Characterization of Phenylacetyl–CoA Ligase from *Pseudomonas putida* ", (1990), Journal of Biological Chemistry, vol. 265, No. 12, pp. 7084–7090.
Kogekar, et al., "Biosynthesis of Penicillin in vitro: Part II–Purification & Properties of 6–Aminopenicillanic Acid- –Phenylacetyl–CoA/Phenoxyacetyl–CoA Transferase", (1983), Indian Journal of Biochemistry & Biophysics, vol. 20, pp. 208–212.
Brunner, et al., "Phenacyl: Coenzyme A Ligase", (1975), Methods in Enzymology, vol. XLIII, pp. 477–481.

* cited by examiner

*Primary Examiner*—Karen Cochrane Carlson
(74) *Attorney, Agent, or Firm*—Zoltan Kerekes; Stephen Venetianer; Charles M. Kinzig

(57) ABSTRACT

A process for preparing an enzyme from *Penicillium chrysogenum* having Phenylacetate-Coenzyme A activity. DNA encoding for the enzyme is also provided and its use in the production of modified strains.

16 Claims, 4 Drawing Sheets

Figure 1

MVFLPPKESGQLDPIPDNIPISEFMLNERYGRVRHASSRDPYTCGITGKSYSSKEVANR
VDSLARSLSKEFGWAPNEGSEWDKTLAVFALNTIDSLPLFWAVHRLGGVLTPANASY
SAAELTHQLLDSKAKALVTCVPLLSISLEAAAKAGLPKNRIYLLDVPEQLLGGVKPPA
GYKSVSELTQAGKSLPPVDELRWSAGEGARRTAFVCYSSGTSGLPKGVMISHRNVIA
NTLQIKAFEQNYRDGGGTKPASTEVALGLLPQSHIYALVVIGHAGAYRGDQTIVLPKF
ELKSYLNAIQQYKISALFLVPPIIIHMLGTQDVCSKYDLSSVTSLFTGAAPLGMETAAD
FLKLYPNILIRQGYGLTETCTVVSSTHPHDIWLGSSGALLPGVEARIVTPENKEITTYD
SPGELVVRSPSVVLGYLNNEKATAETFVDGWMRTGDEAVIRRSPKGIEHVFIVDRIKE
LIKVKGLQVAPAELEAHILAHPDVSDCAVIAIPDDRAGEVPKAIVVKSASAGSDESVS
QALVKYVEDHKARHKWLKGGIRFVDAIPKSPSGKILRRLIRDQEKEARRKAGSKI

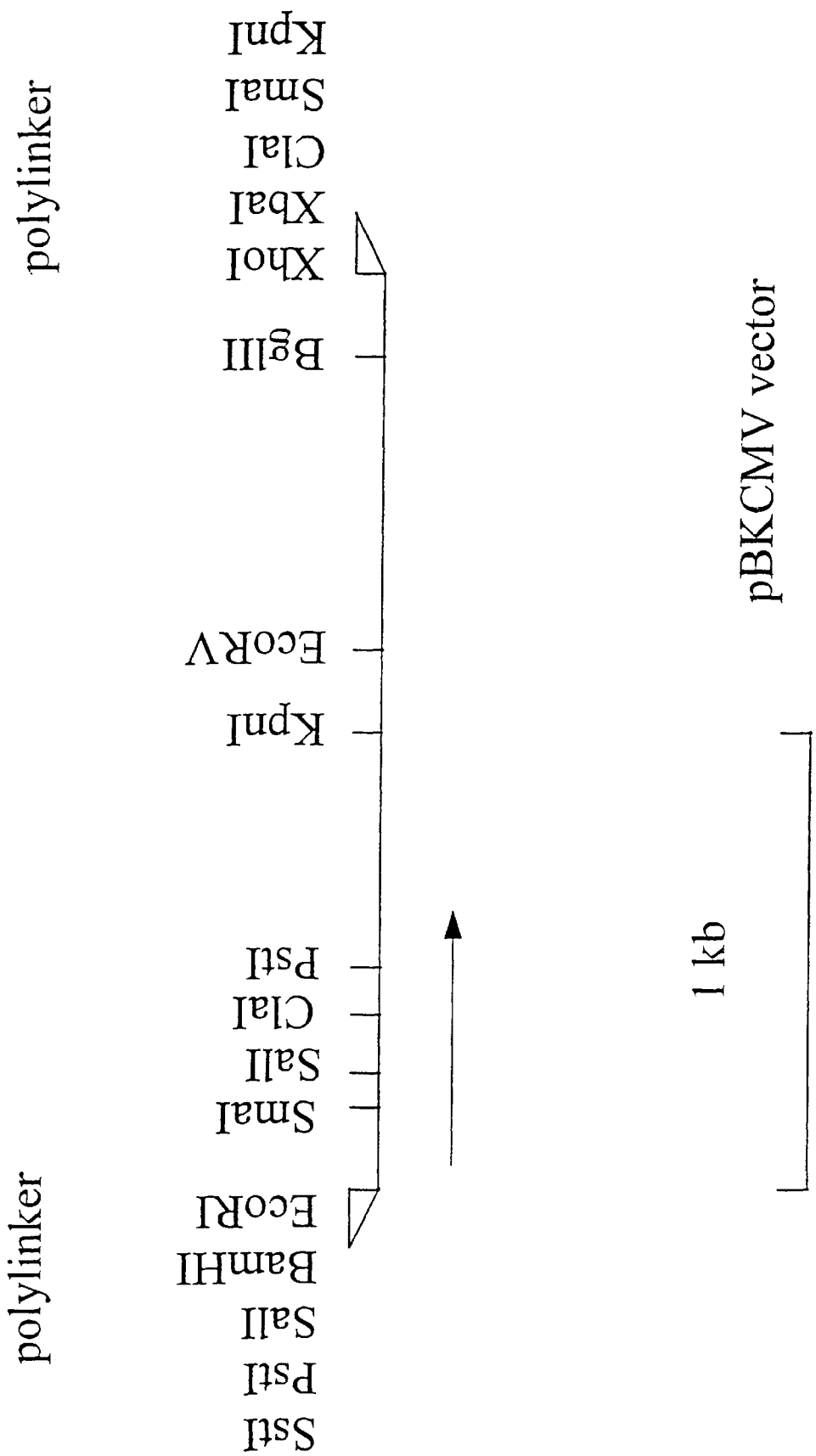
Figure 2. Restriction map of PAA-CoA ligase cDNA clone.

Figure 3

```
GAATTCGGCACGAGTCTAAACCCCGAGATCACCTCAGTTTCCTGCACTTTGGAGA
CCTGCCCCTATATTACCCCGAGGATTTGGGAAAATGGTTTTTTTACCTCCAAAGGA
GTCCGGTCAATTGGACCCAATTCCCGACAATATTCCAATCAGCGAGTTTATGCTCA
ATGAGAGATATGGACGAGTGCGACACGCCAGCTCCCGGGACCCATACACCTGTGG
TATTACCGGGAAGTCATACTCGTCGAAAGAGGTAGCCAATCGCGTCGACTCGCTG
GCTCGTAGTCTATCAAAGGAATTTGGTTGGGCGCCGAATGAAGGGTCAGAATGGG
ATAAGACATTGGCCGTGTTTGCCCTCAACACTATCGATTCCTTACCCCTATTCTGG
GCCGTTCACAGACTGGGCGGTGTTCTCACTCCCGCCAACGCATCATACTCCGCCG
CCGAGCTGACGCATCAGCTGCTTGATTCCAAGGCCAAGGCCCTTGTGACTTGTGT
TCCTCTCCTCTCCATCTCACTGGAAGCTGCAGCCAAAGCTGGTCTCCCGAAGAACA
GAATCTACTTACTCGATGTACCTGAGCAGCTTCTTGGCGGAGTCAAGCCTCCAGC
AGGATACAAGTCCGTTTCCGAACTGACCCAGGCTGGGAAGTCTCTCCCGCCAGTG
GATGAATTGCGATGGAGCGCGGGTGAAGGTGCCCGGCGAACAGCATTTGTGTGCT
ACTCAAGTGGAACGTCTGGATTGCCGAAAGGAGTCATGATCTCACACCGCAACGT
GATCGCCAATACCCTTCAGATCAAGGCGTTTGAGCAGAACTACCGGGATGGTGGG
GGCACAAAGCCTGCGAGTACTGAGGTTGCTCTTGGTCTCCTTCCGCAGAGCCATA
TCTATGCTCTTGTGGTCATTGGCCATGCTGGGGCATACCGAGGCGACCAAACAAT
CGTTCTCCCCAAATTCGAATTGAAATCCTACCTGAACGCCATCCAACAGTACAAG
ATCAGTGCGCTGTTCCTGGTACCTCGATCATCATTCACATGCTGGGCACTCAAGA
CGTGTGCTCCAAGTATGACCTGAGTTCCGTGACGTCTCTGTTCACGGGAGCGGCA
CCCCTGGGTATGGAGACAGCTGCCGATTCCTCAAACTCTACCCGAACATTTTGAT
CCGCCAAGGATACGGTCTGACAGAGACATGCACGGTCGTAAGCTCGACCCACCCG
CACGATATCTGGCTAGGTTCATCCGGCGCTTTGCTCCTGGAGTCGAGGCACGAA
TTGTGACGCCTGAAAACAAGGAAATCACAACGTACGACTCACCGGGCGAATTGGT
GGTCCGAAGCCCAAGCGTCGTCCTGGGCTATTTGAACAACGAAAAAGCCACCGCA
GAGACATTTGTGGACGGATGGATGCGTACGGGAGACGAGGCTGTCATCCGTAGA
AGCCCGAAGGGCATCGAGCACGTGTTTATTGTCGATCGGATCAAGGAGTTGATCA
AGGTCAAGGGTCTGCAAGTCGCGCCTGCCGAACTCGAAGCCCATATCCTCGCCCA
CCCCGATGTCTCGGACTGTGCTGTCATCGCTATTCCGGATGATCGTGCAGGAGAA
GTACCCAAGGCCATTGTTGTGAAGTCCGCCAGCGCAGGATCGGACGAATCTGTCT
CCCAGGCTCTCGTGAAGTATGTTGAGGACCACAAGGCTCGTCACAAGTGGTTGAA
GGGAGGTATCAGATTTGTGGATGCCATTCCCAAGAGCCCGAGTGGTAAGATTCTT
CGTCGGTTGATCCGTGACCAAGAGAAGGAGGCACGGAGAAAGGCTGGTAGCAAG
ATCTAAAAATGTCGGGGGTAGCTTTGATTAGAACTTGGTCTGGGAAACTTGGAAA
CCGATAACCATTGTTGGCTTGAACTAGAAGTATATATGTAAATACGTGATAAACA
AGGCATCTCATCTGCTGTTAAAAAAAAAAAAAAAAAAAAAAACTCGAG
```

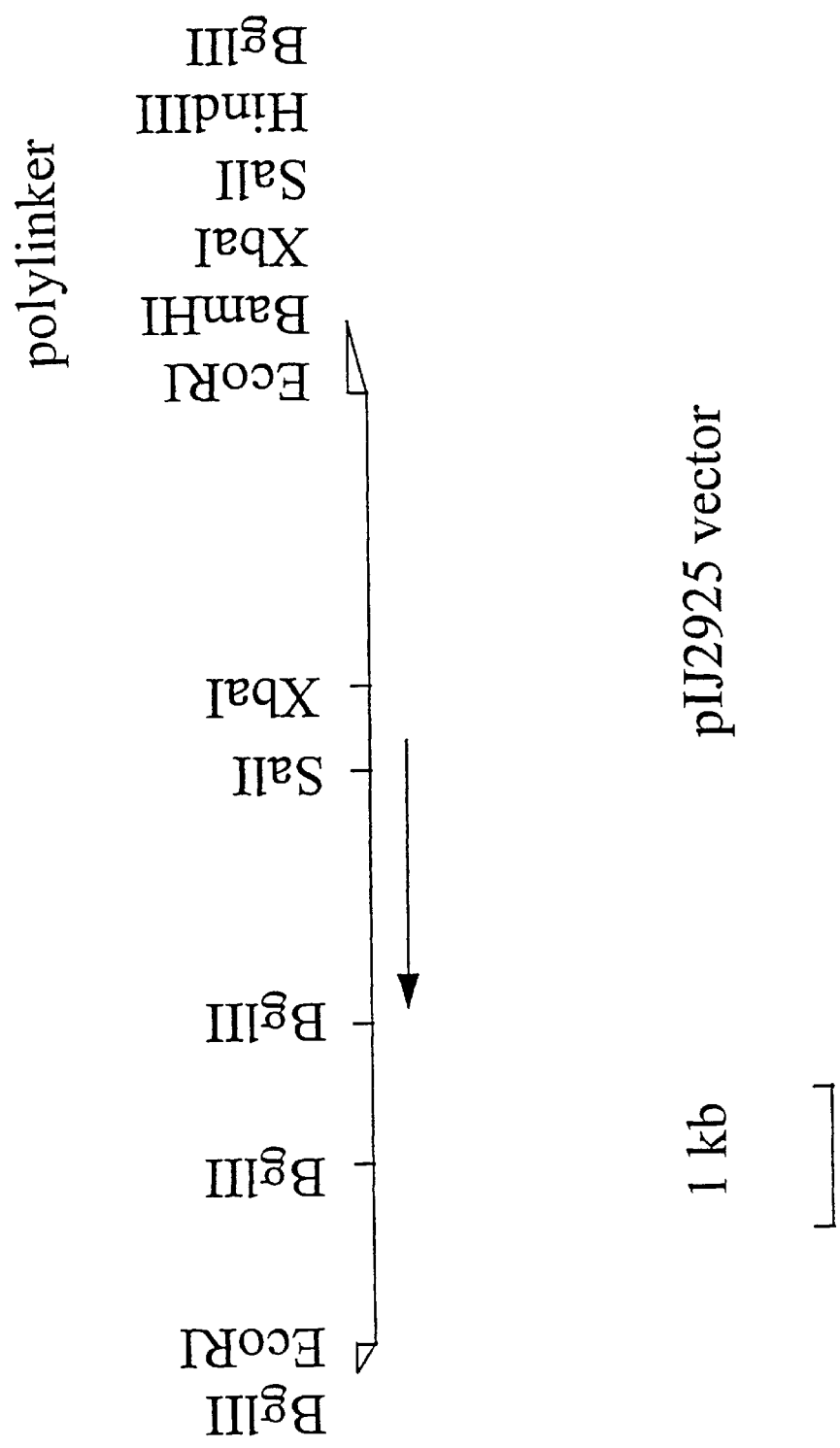
Figure 4. Restriction map of genomic DNA of PAA-CoA ligase

SEQUENCE LISTING

<160> NUMBER OF SEQ ID NOS: 6

<210> SEQ ID NO 1
<211> LENGTH: 578
<212> TYPE: PRT
<213> ORGANISM: Penicillium Chrysogenum

<400> SEQUENCE: 1

```
Met Val Phe Leu Pro Pro Lys Glu Ser Gly Gln Leu Asp Pro Ile Pro
 1               5                  10                  15

Asp Asn Ile Pro Ile Ser Glu Phe Met Leu Asn Glu Arg Tyr Gly Arg
                20                  25                  30

Val Arg His Ala Ser Ser Arg Asp Pro Tyr Thr Cys Gly Ile Thr Gly
             35                  40                  45

Lys Ser Tyr Ser Ser Lys Glu Val Ala Asn Arg Val Asp Ser Leu Ala
         50                  55                  60

Arg Ser Leu Ser Lys Glu Phe Gly Trp Ala Pro Asn Glu Gly Ser Glu
 65                  70                  75                  80

Trp Asp Lys Thr Leu Ala Val Phe Ala Leu Asn Thr Ile Asp Ser Leu
                 85                  90                  95

Pro Leu Phe Trp Ala Val His Arg Leu Gly Gly Val Leu Thr Pro Ala
                100                 105                 110

Asn Ala Ser Tyr Ser Ala Ala Glu Leu Thr His Gln Leu Leu Asp Ser
            115                 120                 125

Lys Ala Lys Ala Leu Val Thr Cys Val Pro Leu Leu Ser Ile Ser Leu
        130                 135                 140

Glu Ala Ala Lys Ala Gly Leu Pro Lys Asn Arg Ile Tyr Leu Leu
145                 150                 155                 160

Asp Val Pro Glu Gln Leu Leu Gly Gly Val Lys Pro Pro Ala Gly Tyr
                165                 170                 175

Lys Ser Val Ser Glu Leu Thr Gln Ala Gly Lys Ser Leu Pro Pro Val
            180                 185                 190

Asp Glu Leu Arg Trp Ser Ala Gly Glu Gly Ala Arg Arg Thr Ala Phe
        195                 200                 205

Val Cys Tyr Ser Ser Gly Thr Ser Gly Leu Pro Lys Gly Val Met Ile
    210                 215                 220

Ser His Arg Asn Val Ile Ala Asn Thr Leu Gln Ile Lys Ala Phe Glu
225                 230                 235                 240

Gln Asn Tyr Arg Asp Gly Gly Thr Lys Pro Ala Ser Thr Glu Val
                245                 250                 255

Ala Leu Gly Leu Leu Pro Gln Ser His Ile Tyr Ala Leu Val Val Ile
            260                 265                 270

Gly His Ala Gly Ala Tyr Arg Gly Asp Gln Thr Ile Val Leu Pro Lys
        275                 280                 285

Phe Glu Leu Lys Ser Tyr Leu Asn Ala Ile Gln Gln Tyr Lys Ile Ser
    290                 295                 300

Ala Leu Phe Leu Val Pro Pro Ile Ile Ile His Met Leu Gly Thr Gln
305                 310                 315                 320

Asp Val Cys Ser Lys Tyr Asp Leu Ser Ser Val Thr Ser Leu Phe Thr
                325                 330                 335

Gly Ala Ala Pro Leu Gly Met Glu Thr Ala Ala Asp Phe Leu Lys Leu
            340                 345                 350

Tyr Pro Asn Ile Leu Ile Arg Gln Gly Tyr Gly Leu Thr Glu Thr Cys
```

|     |     |     |     | 355 |     |     |     |     | 360 |     |     |     |     | 365 |     |
| --- | --- | --- | --- | --- | --- | --- | --- | --- | --- | --- | --- | --- | --- | --- | --- |
| Thr | Val | Val | Ser | Ser | Thr | His | Pro | His | Asp | Ile | Trp | Leu | Gly | Ser | Ser |
|     |     |     |     | 370 |     |     |     |     | 375 |     |     |     |     | 380 |     |

Gly Ala Leu Leu Pro Gly Val Glu Ala Arg Ile Val Thr Pro Glu Asn
385                 390                 395                 400

Lys Glu Ile Thr Thr Tyr Asp Ser Pro Gly Glu Leu Val Val Arg Ser
                405                 410                 415

Pro Ser Val Val Leu Gly Tyr Leu Asn Asn Glu Lys Ala Thr Ala Glu
            420                 425                 430

Thr Phe Val Asp Gly Trp Met Arg Thr Gly Asp Glu Ala Val Ile Arg
            435                 440                 445

Arg Ser Pro Lys Gly Ile Glu His Val Phe Ile Val Asp Arg Ile Lys
450                 455                 460

Glu Leu Ile Lys Val Lys Gly Leu Gln Val Ala Pro Ala Glu Leu Glu
465                 470                 475                 480

Ala His Ile Leu Ala His Pro Asp Val Ser Asp Cys Ala Val Ile Ala
            485                 490                 495

Ile Pro Asp Asp Arg Ala Gly Glu Val Pro Lys Ala Ile Val Val Lys
            500                 505                 510

Ser Ala Ser Ala Gly Ser Asp Glu Ser Val Ser Gln Ala Leu Val Lys
515                 520                 525

Tyr Val Glu Asp His Lys Ala Arg His Lys Trp Leu Lys Gly Gly Ile
530                 535                 540

Arg Phe Val Asp Ala Ile Pro Lys Ser Pro Ser Gly Lys Ile Leu Arg
545                 550                 555                 560

Arg Leu Ile Arg Asp Gln Glu Lys Glu Ala Arg Arg Lys Ala Gly Ser
            565                 570                 575

Lys Ile

<210> SEQ ID NO 2
<211> LENGTH: 1976
<212> TYPE: DNA
<213> ORGANISM: Penicillium Chrysogenum

<400> SEQUENCE: 2

```
gaattcggca cgagtctaaa ccccgagatc acctcagttt cctgcacttt ggagacctgc    60
ccctatatta ccccgaggat ttgggaaaat ggttttttta cctccaaagg agtccggtca   120
attggaccca attcccgaca atattccaat cagcgagttt atgctcaatg agagatatgg   180
acgagtgcga cacgccagct cccgggaccc atacacctgt ggtattaccg ggaagtcata   240
ctcgtcgaaa gaggtagcca atcgcgtcga ctcgctggct cgtagtctat caaaggaatt   300
tggttgggcg ccgaatgaag ggtcagaatg ggataagaca ttggccgtgt ttgccctcaa   360
cactatcgat tccttacccc tattctgggc cgttcacaga ctgggcggtg ttctcactcc   420
cgccaacgca tcatactccg ccgccgagct gacgcatcag ctgcttgatt ccaaggccaa   480
ggcccttgtg acttgtgttc ctctcctctc catctcactg gaagctgcag ccaaagctgg   540
tctcccgaag aacagaatct acttactcga tgtacctgag cagcttcttg cggagtcaa    600
gcctccagca ggatacaagt ccgtttccga actgacccag gctgggaagt ctctcccgcc   660
agtggatgaa ttgcgatgga gcgcgggtga aggtgcccgg cgaacagcat tgtgtgcta    720
ctcaagtgga acgtctggat tgccgaaagg agtcatgatc tcacaccgca acgtgatcgc   780
caatacccct cagatcaagg cgtttgagca gaactaccgg gatggtgggg gcacaaagcc   840
```

```
tgcgagtact gaggttgctc ttggtctcct tccgcagagc catatctatg ctcttgtggt    900
cattggccat gctggggcat accgaggcga ccaaacaatc gttctcccca aattcgaatt    960
gaaatcctac ctgaacgcca tccaacagta caagatcagt gcgctgttcc tggtacctcc   1020
gatcatcatt cacatgctgg gcactcaaga cgtgtgctcc aagtatgacc tgagttccgt   1080
gacgtctctg ttcacgggag cggcacccct gggtatggag acagctgccg atttcctcaa   1140
actctacccg aacattttga tccgccaagg atacggtctg acagagacat gcacggtcgt   1200
aagctcgacc cacccgcacg atatctggct aggttcatcc ggcgctttgc tccctggagt   1260
cgaggcacga attgtgacgc ctgaaaacaa ggaaatcaca acgtacgact caccgggcga   1320
attggtggtc cgaagcccaa gcgtcgtcct gggctatttg aacaacgaaa agccaccgc    1380 agagacattt gtggacggat ggatgcgtac gggagacgag gctgtcatcc gtagaagccc   1440
gaagggcatc gagcacgtgt ttattgtcga tcggatcaag gagttgatca aggtcaaggg   1500
tctgcaagtc gcgcctgccg aactcgaagc ccatatcctc gcccacccg atgtctcgga    1560 ctgtgctgtc atcgctattc cggatgatcg tgcaggagaa gtacccaagg ccattgttgt   1620
gaagtccgcc agcgcaggat cggacgaatc tgtctcccag gctctcgtga agtatgttga   1680
ggaccacaag gctcgtcaca agtggttgaa gggaggtatc agatttgtgg atgccattcc   1740
caagagcccg agtggtaaga ttcttcgtcg gttgatccgt gaccaagaga aggaggcacg   1800
gagaaaggct ggtagcaaga tctaaaaatg tcggggtag ctttgattag aacttggtct    1860
gggaaacttg gaaccgata accattgttg gcttgaacta aagtatata tgtaaatacg     1920 tgataaacaa ggcatctcat ctgctgttaa aaaaaaaaa aaaaaaaaa ctcgag         1976
```

<210> SEQ ID NO 3
<211> LENGTH: 13
<212> TYPE: PRT
<213> ORGANISM: Penicillium Chrysogenum

<400> SEQUENCE: 3

Val Phe Leu Pro Pro Lys Glu Ser Gly Gln Leu Asp Pro
 1               5                  10

<210> SEQ ID NO 4
<211> LENGTH: 22
<212> TYPE: DNA
<213> ORGANISM: Penicillium Chrysogenum

<400> SEQUENCE: 4
acaggaaaca gctatgacct tg                                             22

<210> SEQ ID NO 5
<211> LENGTH: 155
<212> TYPE: DNA
<213> ORGANISM: Penicillium Chrysogenum

<400> SEQUENCE: 5
tctaaacccc gagatcacct cagtttcctg cactttggag acctgcccct atattacccc    60
gaggatttgg gaaaatggtt tttttacctc caaaggagtc cggtcaattg gacccaattc   120
ccgacaatat tccaatcagc gagtttatgc tcaat                               155

<210> SEQ ID NO 6
<211> LENGTH: 27
<212> TYPE: PRT
<213> ORGANISM: Penicillium Chrysogenum

```
<400> SEQUENCE: 6

Met Val Phe Leu Pro Pro Lys Glu Ser Gly Gln Leu Asp Pro Ile Pro
 1               5                  10                  15

Asp Asn Ile Pro Ile Ser Glu Phe Met Leu Asn
             20                  25
```

PHENYLACETYL-COA LIGASE FROM PENICILLIUM CHRYSOGENUM

This application is a national stage application (35 U.S.C. 371) of PCT/EP96/02799, filed Jun. 26, 1996 which claims priority to Great Britain application Ser. No. 9513403.7, filed Jun. 30, 1995.

The present invention relates to an enzyme useful in the synthesis of penicillins from intermediates involved in penicillin biosynthesis. The present invention also relates to processes for the preparation of the enzyme and DNA coding for the enzyme.

The biochemical pathway for Penicillin G is disclosed in the literature (Queener (1990) Antimicrobial Agents and Chemotherapy 34(6), 943–948; Martin (1992) J. Industrial Microbiol 9, 73–90; Luengo (1995) J. Antibiotics 48 (11), 1195–1212). The pathway has been the subject of considerable study with a view to increasing the yield (titre) in fermentation processes.

Phenylacetate (PAA) and Phenoxyacetate (POA) are activated to the corresponding CoA thioesters in *Penicillium chrysogenum* by a ligase enzyme (e.g. PAA-CoA ligase). These thioesters are then used for the biosynthesis of Penicillin G in the case of PAA and penicillin V in the case of POA. PAA-CoA ligase is therefore thought to be essential in the biosynthesis of these commercially important therapeutic antibiotics.

An enzyme from *Pseudomonas putida* having PAA-CoA ligase activity has been isolated (J. Biol. Chem. 267(12), 7084–7090 (1990) in a purification procedure involving ammonium sulphate precipitation and potassium chloride elution from a DEAE-Sephacel column. The enzyme has a molecular weight of 48 kDa +/−1 kD, a pH optimum of 8.2 and is involved in PAA catabolism.

Attempts to assay an enzyme having PAA-CoA ligase activity from *P. chrysogenum* by the hydroxymate method (a colorimetric assay detecting phenylacetyl-hydroxamate or phenoxyacetyl-hydroxamate at 540 nm) have been reported by Kogekar & Deshpande (1983) Ind. J. Biochem. Biophys 20, 208–212 and by Brunner & Rohr (1975) Methods Enzymol 43, 476–481; however other workers (Martinez-Blanco et al (1992) J. Biol. Chem. 26(8), 5474–5481) are of the view that the protein had not been purified or the activity characterised in detail. Moreover the latter authors failed to find the enzyme by the reported procedure.

WO 96/10085 (Gist Brocades, published Apr. 4, 1996) reviews these and other attempts at isolating a PAA CoA ligase which operates in the penicillin pathway. In WO 96/10085 an acyl-CoA enzyme synthetase is described as being obtained from a strain of *Penicillium chrysogenum* B 10 which is held by PanLabs (USA). Among the specific properties attributed to the enzyme are the following: molecular weight about 50 kDa (as determined by gel filtration), pH optimum pH 8 to 8.5 (low activity at pH 7 or below), temperature optimum at 40° C., pI higher than 7.25. Importantly the enzyme can be purified by ammonium sulphate precipitation. It has a fairly wide specificity (ie. it is able to catalyze the formation of phenoxyacetyl-coenzyme A, phenylacetyl-coenzyme A, adipyl-coenzyme A and hexanoyl-coenzyme A from Mg 2+, ATP, CoASH, and phenoxyacetic acid, phenylacetic acid, adipic acid or hexanoic acid respectively but does not show any significant activity towards acetic acid. Also it is said that the enzyme is stabilised by reducing agents. A high concentration of ammonium sulphate or glycerol also stabilises the enzyme. No indications of purity are given for the enzyme activity obtained by the methods disclosed and no sequence or N-terminal sequence is given for the enzyme and the corresponding DNA is not characterised or its sequence given.

In spite of all these efforts little is known about the authentic PAA-CoA ligase enzyme that operates in Penicillium sp. in vivo . It had been speculated that the enzyme responsible may be involved in primary metabolism (Smith et al (1990) Biotechnology 8, 39–41). Martinez-Blanco et al (1992) ibid selected one possible candidate enzyme, acetyl CoA synthetase, and purified it from *P. chrysogenum* on the basis of acetyl CoA synthetase activity. They were able to show that in addition to forming the CoA derivative of acetate, acetyl CoA synthetase was able to activate several fatty acids (C2 –C8) and some aromatic molecules (including PAA) in vitro.

The acetyl CoA synthetase gene has been sequenced (International Patent WO92/07079, Gouka et al (1993) Appl. Microbiol. Biotechnol. 3, 514–519, Martinez-Blanco et al (1993) Gene 130, 265–270) and has been shown to have homology with other acetyl CoA synthetases from fungi. However mutations in this gene selected by fluoroacetic acid do not appear to alter penicillin production levels (International Patent WO92/07079) suggesting that in vivo another enzyme is actually responsible for activation of PAA.

In the present invention a direct assay for PAA-CoA ligase activity has been developed in conjunction with a specific purification protocol and this has allowed purification of and subsequent cloning of what is believed to be the authentic PAA-CoA ligase. The enzyme isolated by the present invention has a different N-terminal amino acid sequence to the acetyl CoA synthetase mentioned above and possesses a number of different properties (e.g. molecular weight) indicating that a different enzyme has been isolated from all the enzymes attributed with this role to date. The properties characteristic of the enzyme isolated in the present invention include an absolute dependence on CoASH as substrate while the enzyme isolated by Kogekar & Deshpande (1983) ibid was assayed in conditions where CoASH was omitted. This and other differences between the isolated proteins (e.g. pH optima and other characteristics given in the examples below) show that the enzyme in the present invention is different to any of those described in the prior art. It is believed that the present work represents the first isolation of a pure form of the enzyme PAA CoA ligase from Penicillium sp. In particular the presence of an SKI C-terminal peptide is consistent with this enzyme having a real role in penicillin biosynthesis. The enzyme of the present invention differs from that in WO 96/10085 mentioned above in that it has a different molecular weight and the enzyme of the present invention, unlike that of WO 96/10085 is sensitive to ammonium sulphate precipitation and chloride salts.

Accordingly, the present invention provides an enzyme having PAA-CoA ligase activity obtainable from *Penicillium chrysogenum* by culturing, harvesting and sonicating the mycelium, removing cell debris and fractionating the sonicate by anion-exchange chromatography, followed by hydrophobic interaction chromatography, affinity chromatography with substrate elution and gel filtration chromatography wherein the active chromatographic fractions are detected using a PAA and coenzyme A dependent assay.

The enzyme is preferably in purified form, advantageously in substantially pure form.

The enzyme of this invention has an apparent molecular mass of 63 kDa (by SDS PAGE)

Preferably the enzyme includes the sequence of N-terminal amino acids

VFLPPKESGQLDP

In particular, the enzyme comprises the sequence of amino acids in FIG. 1/ID SEQ 1

In a further aspect of the invention there is provided a method of preparing an enzyme having PAA-CoA ligase activity by culturing Penicillium sp. followed by extraction and purification wherein the active fractions are detected using a PAA and Co-enzyme A dependent assay. In particular the Penicillium sp. is *P. chrysogenum* and the mycelium is treated by sonication, followed by fractionation by anion-exchange, hydrophobic interaction, affinity and gel filtration chromatography so as to provide an approximate 1000 fold increase in purity.

The enzyme can be used in in vitro biotransformations. For example for CoA ester synthesis or for penicillin synthesis when mixed with acyl-CoA: 6-APA acyltransferase. The in vitro biotransformations can be carried out using whole cells, cell free extracts, permeabilised cells or the isolated enzyme from the microorganisms or any of these in immobilised form.

Where the biotransformation is carried out using whole cells, the microorganism may be in the form of a growing culture, resting culture, washed mycelium, immobilised cells or protoplasts.

When cell-free extracts are used these are suitably produced by shear and /or chemical or enzymic lysis or other methods of disruption, preferably sonication, and optionally thereafter removing cell debris, leaving the enzyme activity in solution.

The enzyme is suitably prepared according to the examples below using commercially available strains of *P. chrysogenum* including wild type NRRL 1 95 1. Other suitable strains of *P. chrysogenum* include high penicillin producing strains e.g. strain BW1901 (EMBO J. 9(3), 741–747 (1990) D. J. Smith et al.).

The enzyme may be prepared by culturing the microorganism in a conventional manner, especially under aerobic conditions in a suitable liquid or semi-solid medium. The culture conditions may be a temperature in the range from 5–50° C. preferably 25–30° C. and pH in the range 3 to 9, preferably 6–8, most preferably 7.2.

The enzyme may be isolated and used in purified form, partially purified form, as obtained in an impure state, as a filtrate from a disrupted cell preparation, as a crude cell homogenate and so on. Most suitably the enzyme is, for example, at least purified to remove other enzymes which might also catalyse the destruction of the starting materials or the enzyme.

Most suitably the enzyme is immobilised for example to an insoluble support material such as by the procedures discussed by Powell (1990) in Microbial Enzymes and Biotechnology ed. Fogarty & Kelly p369–394. This provides the advantage of increased yield and throughput.

When the biotransformation is carried out using whole cells, a suitable incubation medium comprises medium: $KH_2PO4$ 2 g, $K_2HPO_4$ 1.5 g, KCl 0.2 g, Mg $Cl_2.6H_2O$ 0.2 g, $Na_2SO_4.10H_2O$ 0.22 g, glucose 1.0 g in a liter of deionised water pH 6.5 or a water system with pH adjustment.

When the biotransformation is carried out using cell free extracts the incubation medium comprises a suitable buffer. In addition to substrates the enzyme reaction mixture may contain one or more other cofactors e.g. metal ions or stabilisers. for example thiols.

The biotransformation may suitably be carried out in aqueous media, the reaction mixture suitably being maintained in the range pH 4–10, more suitably from 6 to 10, preferably around 9.0. The pH is suitably controlled using buffers or preferably by the addition of acid or base titrant. The temperature of the reaction should generally be in the range 5–50° C. preferably 22–45° C., most preferably 30–37° C. Alternatively the reaction can be carried out in organic solvents or in the presence of organic solvents e.g. acetone, methyl isobutyl ketone (MIBK).

The reaction time depends on such factors as concentrations of reactants and cofactors, temperature and pH. After the reaction is complete the product can be isolated by conventional methods. The initial purification conveniently involves a chromatography step.

In a further aspect the present invention also provides DNA encoding the PAA-CoA ligase of the present invention. The gene encoding said protein is located within the DNA fragment shown in FIG. 2. In particular the DNA comprises substantially the DNA sequence in FIG. 3/ID SEQ 2.

In FIG. 2 the approximate length in kilobases (kb) of the DNA as determined by sizing experiments carried out by agarose gel electrophoresis, is indicated. It should be understood that the figure is not intended to show all the restriction sites present on the DNA.

It will be understood that the DNA of this invention is not in its natural state as it occurs in nature but is in isolated or substantially pure form. It will be understood that the invention encompasses DNA which may not have the precise configuration of restriction sites illustrated if the said DNA has been derived by standard techniques including nucleotide deletion, substitution, addition or inversion from the DNA according to any aspect of the invention described above.

Preferably the DNA of the present invention is derived from *P. chrysogenum*. However the invention also encompasses DNA sequences derived from other suitable organisms especially producing organisms other than *P. chrysogenum* which sequences do not have the configuration of restriction sites shown but which hybridise, preferably under conditions of high stringency, with the DNA shown in FIG. 2 or a subfragment thereof and which code for PAA-CoA ligase or an enzyme with PAA-CoA ligase activity (high stringency conditions are for example, as given in Example 18).

The invention also provides a vector comprising such DNA, preferably an expression vector for expressing PAA-CoA ligase in a suitable host organism. A specific example of such an expression vector is pBK-CMV (purchased from Stratagene) and used in this invention for expression in *E. coli*. In this invention the cDNA insert of PAA-CoA ligase (=pPEN09, FIG. 2) is a preferred vector for expression in *E. coli*.

The DNA of the invention and vectors containing same may find use in many areas of industrial activity. That also applies to host micro-organisms transformed with said vectors and the enzymes they express. For example the DNA may be utilised as a hybridization probe to identify and isolate related or overlapping genes present on the total cellular DNA of *P. chrysogenum* (NRRL 195 1) and of other micro-organisms which produce enzymes of similar structure and specificity.

Recombinant vectors containing said DNA may be of value, when transformed into suitable hosts, in the production of genetically modified micro-organisms which synthesize increased amounts of penicillin.

It would be very advantageous to increase the amount of activity of PAA-CoA ligase in a suitable organism. Recombinant vectors could also be used in the generation of novel or hybrid antibiotics via the process of gene transfer (see for example D. A. Hopwood et al, Nature, 1985, 314, 642–644). Enzymes encoded by the DNA of the invention may be used, for example, in cell-free systems especially when immobilised on suitable solid supports, to prepare the known antibiotic from natural precursors or a novel antibiotic from 'unnatural' precursors obtained, for example, by chemical synthesis.

The DNA of the invention or a fragment thereof (not necessarily carrying an intact gene) may be combined, either by recombinant DNA techniques or by natural recombination processes, with a fragment of a gene involved in biosynthesis to produce a hybrid gene capable of directing the synthesis of a hybrid enzyme. Such enzymes may be used in the production of novel antibiotics by processes analogous to those hereinbefore described.

The DNA of the invention may also be modified by the known techniques of site-directed mutagenesis (in a manner analogous to that described, for example, by G. Winter et al, Nature, 1982, 299, 756–758; or by Zoller and Smith, Nucleic Acids Research, 1982, 10, 6487–6500) to give DNA in which specific mutations and/or deletions have been effected. The mutated DNA may be used to obtain an increased yield (or titre) of penicillin from a suitable host micro-organism.

The mutated DNA may also be used to obtain novel or hybrid antibiotics by gene transfer, or used in the production of mutant enzymes (muteins) which may be used in the production of novel antibiotics by analogous processes to those hereinabove described. The mutated DNA may also be used to alter other fermentation properties of suitable organisms e.g. PAA tolerance, altered substrates.

The following examples illustrate the invention.

EXAMPLE 1
*P. chrysogenum* Fermentation

Spores of *Penicillium chrysogenum* (SmithKline Beecham Strain BW1901) was inoculated into 15 ml of PVS media (35 g/l corn steep liquor, 15 g/l glucose, 5 g/l $CaCO_3$, 8 ml/1 rape seed oil, pH to 5.9 with NaOH) in 100 ml shake flask. The culture was grown for 48 h at 26° C. with orbital shaking (230 rpm) before taking 1 ml of whole broth and transferring to 10 ml of C5 media (35 g/l corn steep liquor, 85 g/l lactose, 10 g/l $CaCO_3$, 10 g/l $NaH_2PO_4$, 8 g/l$(NH_4)_2SO_4$, 4 g/l $MgSO_4.7H_2O$, 4 g/l $Na_2SO_4$, 6 ml/1 rape seed oil, 6 g/l phenoxyacetic acid, pH to 6.0 with NaOH) in 100 ml shakeflask. This culture was then grown for 55 h at 26° C. with orbital shaking (230rpm) before harvesting the mycelia.

EXAMPLE 2
Preparation of Protein Extracts from *P. chrysogenum* for Assay, Purification and Western Blotting of PAA-CoA Ligase.

Mycelia from a 55 h C5 shakeflask cultured as described in example 1 was harvested by filtering through glass microfibre filters (Whatman GFIA). The mycelial mat was washed with 300 ml of 0.9% (w/v) sodium chloride (4° C.) and then scraped from the filter and placed into 10 ml Ligase assay buffer (30 mM Tris-HCl pH 9.0, 1 mM dithiothreitol, 100 μg/ml Pefabloc™ in 50% glycerol). The mycelia was then sonicated on ice (3×15 s burst using an Ultrasonics model W-385 sonicator, power setting 5, cycle rate 5 s, 50% duty cycle), and then the mycelial debris was pelleted by centrifugation (18000xg, 4° C. 30 min). The supernatant was frozen at minus 70° C. for storage or used immediately for PAA-CoA Ligase assay, purification or Western blotting (example 7).

EXAMPLE 3
In-Vitro Assay for PAA-CoA Ligase.

To demonstrate the presence of PAA-CoA Ligase activity in extracts or column fractions, 20 μl were mixed with 0.1M phenylacetic acid in 50 mM Tris-HCl pH 7.5 (20 μl), 0.1M sodium ATP (10 μl), 0.2M magnesium chloride (10 μl), 0.02M sodium coenzyme A (10 μ) and 0.015M dithiothreitol (10μl) in plastic eppendorf tubes. The tubes were vortex mixed (5 s) and then placed in a water bath at 30° C. for 15 min. Methanol (100 μl) was then added to the mixtures and the tubes were centrifuged (14K, 1 min) to precipitate the proteins. The supernatant fractions were analysed for the presence of PAA-CoA by HPLC (example 4). In each set of assays a protein extract prepared from a *P. chrysogenum* shakeflask fermentation (example 1) was assayed as a positive control along with a PAA-CoA standard.

EXAMPLE 4
HPLC Analysis of Assay Supernatants.

Supernatant samples from the PAA-CoA Ligase assays (example 3) were analysed for the presence of PAA-COA using a Waters LCMI HPLC system. Samples (100 μl) were injected onto a Radial Pak C18 compression column at room temperature with a flow rate of 2.5 ml/min using a mobile phase of 0.2M sodium phosphate pH 5.4 (Buffer A) isocratically from 0–4 min. This was followed by a linear gradient to 100 % buffer B containing 0.16M sodium phosphate pH 5.4 in 40 % acetonitrile (4–10 min). Buffer B was maintained at 100% for a further 2 min and then the system was re-equilibrated ready for the next injection using a linear gradient back to 100% A (12–13 min). Peaks were detected at 260 nm and PAA-CoA had a retention time of 12 min. Positive samples were those that had co-eluting peaks with the PAA-CoA standard and showed the same UV absorbance spectra as the standard as determined by a photodiode array spectrometer.

EXAMPLE 5
Purification of PAA-CoA Ligase

Care was required as the enzyme activity was found to be extremely labile. Attempts at precipitation of the enzyme with ammonium sulphate were unsuccessful as no activity could be found in the material obtained. This in itself distinguishes the present enzyme from that described in WO 96/10085 (Gist-Brocades).

Unless otherwise stated the following procedure was conducted at 4° C. using buffer C containing 30 mM Tris-HCl, 4 mM DTT, 4 mM EDTA, 5 mM $MgCl_2$ and 20% glycerol (v/v) at pH 9.0. Separations were achieved using a Pharmacia Hi-Load™ system. Cell free extract (500 ml), made as given in example 1, was thawed slowly at 4° C. The extract was then adjusted to pH 9.0 using 5M NaOH with stirring on ice. To this stirring extract was added 275 g of Q-Sepharose Fast Flow (Pharmacia) ion exchange media which had been previously washed with 3l of water followed by 1l of buffer C. This mixture was stirred for 1.5 h on ice. The slurry was then filtered through a further 50 g of washed Q-Sepharose resin on a glass sinter using reduced pressure. The resin was then washed with a further 100 ml of buffer C and then allowed to run dry giving 600 ml of clear extract containing PAA-CoA ligase. Ammonium sulphate (92.4 g ie. subprecipitation levels) was then added and the solution was stirred on ice for 1 h followed by filtration (0.45 μm filter, Millipore, type HA).

The PAA-CoA Ligase extract (700ml) was then loaded at 1 ml/min onto a Phenyl-sepharose 6 Fast Flow, low substitution column (Pharmacia, 12 cm×2.6 cm diameter) previously conditioned with 1l of buffer D (as for buffer C with 140 g/l of ammonium sulphate). The loaded column was then washed with 230 ml of buffer D at 0.8ml/min and then eluted with a linear gradient from 100% buffer D to 100% buffer C over 238 ml at 0.8 ml/min. 5.5 ml fractions were collected and tested for PAA-CoA ligase activity as given in example 3. Active fractions, 41 to 49 were pooled giving 50 ml, which was loaded at 0.5 ml/min onto a 5 ml HiTrap™ Blue affinity column (Pharmacia) previously washed with 50 ml of buffer C. The loaded column was washed with 15 ml of buffer C and then eluted using a linear gradient from 100% buffer C to 100% buffer E over 25 ml at 0.5 ml/min. Buffer E was as for buffer C with the addition of phenylacetic acid to given a final concentration of 0.5M which was re-adjusted to pH 9.0 using solid NaOH. Elution from the affinity column using the natural substrate was used to increase purification selectivity and to enable the enzyme activity to be measured in the resulting fractions. NaCl elution proved unsuccessful because this salt inhibited enzyme activity. In contrast the enzyme described in WO 96/10085 appears to be stable when eluted in KCl.

Active fractions 21, 22 and 23 were pooled to give 6ml, which was then separated at 0.25 ml/min on a Sephacryl S-200 High Performance size exclusion column (Pharmacia, 64 cm×2.6 cm diameter) which had been previously equilibrated in Buffer F (as for buffer C with adjustment to pH 7.5 with 5M HCl). Active fractions 54 to 65 were pooled to give 11 ml which was concentrated down to 60 µl by centrifugal ultrafiltration (Centricon 10,000 MW cut-off, Amicon Inc.). Analysis of the fractions from the size exclusion column by SDS-polyacrylamide gel electrophoresis (example 6) showed a protein of 63 kDa, the intensity of which correlated with PAA-CoA ligase activity. Western Blotting (example 6) was used to complete the purification and to enable N-terminal amino acid sequencing of the PAA-CoA Ligase.

EXAMPLE 6
Western Blotting of PAA-CoA Ligase Protein.

To provide material for N-terminal amino acid sequencing the purified protein (60 µl, example 5) was mixed with an equal volume of SDS-PAGE sample buffer containing 0.5M Tris-HCl pH6.8 (10 ml), sodium dodecyl sulphate (2 g, ultrapure), 2-mercaptoethanol (1 ml), glycerol (10 ml), distilled deionised water (7ml) and 0. 1% bromochlorophenol blue (2 ml). This mixture was boiled for 10 min and allowed to cool to room temperature. Aliquots (5, 15 and 20 µl) were loaded on to a 10% polyacrylamide gel (4% stacking gel) cast into a Bio-Rad Mini Protean II electrophoresis cell prepared using the Manufacturers protocol. Electrophoresis was conducted in electrode buffer containing 0.025M Tris, 0.192M glycine and 0.1% w/v sodium dodecyl sulphate (ultrapure) at 200V for 45 min after which time the polyacrylamide gel was placed in to electroblotting buffer (10 mM 3-[cyclohexylamino]-1-propanesulfonic acid, pH11 in 10% methanol) for 5 min. Proteins in the polyacrylamide gel were transferred on to Applied Biosystems ProBlott™ immobilisation membrane using a Bio-Rad Mini Trans-Blot electrophoretic transfer cell following the Applied Biosystems protocol. On completion of blotting the membrane was stained with Coomassie Blue R-250 using the staining method in the Applied Biosystems protocol. The protein band at 63 kDa was cut from the membrane and this material was used for N-terminal amino acid sequencing (example 7).

EXAMPLE 7
N-terminal Amino Acid Sequencing

N-terminal amino acid sequence was obtained from blotted protein (example 6) using an Applied Biosystems (ABI) 477A Pulsed Liquid Sequencer. Sequence was obtained using standard Edman Chemistry with identification of released PTH-labelled amino acids using ABI 120 Å narrowbore chromatography. Analysis of the purified PAA-CoA ligase protein resulted in the following sequence assignment:

V-F-L-P-P-K-E-S-G-Q-L-D-P

EXAMPLE 8
Synthesis of PAA-CoA Ligase N-Terminal Peptide.

The N-terminal amino acid sequence determined from the 63 kDa PAA-CoA Ligase protein (example 7) was used to synthesise a peptide. This was synthesized by Peptide and Protein Research Consultants (Washington Singer Laboratories, University of Exeter, Perry Road, Exeter, Devon EX4 4QG, UK) as 50 mg free peptides. 12 mg was conjugated to maleimide activated BSA (Bovine Serum Albumin) using SMCC (Succinimidyl 4-(N-maleimidomethyl)cyclohexane-1 -carboxylate) and 2.5 mg was conjugated to maleimide activated OVA (Ovalbumin) using MBS (m-Maleimidobenzoyl-N-hydroxysuccinimide ester).

EXAMPLE 9
Production of Polyclonal Antibodies to Peptide Derived from the N-Terminus of the 63 kDa PAA-CoA Ligase Protein.

Peptide conjugated to BSA (example 8) was used for the production of rabbit polyclonal antibodies specific to the 63 kDa PAA-CoA Ligase protein. The peptide-BSA conjugate (375 µg/ml) was filter sterilised (0.2 µm filter) and 1 ml of the sterile solution was thoroughly mixed with 2 ml of non-ulcerative Freunds complete adjuvant (Brian Morris International, Guildford U.K). A total of 0.8 ml of this mixture (100 µg of the peptide-BSA conjugate) was administered sub-cutaneously to New Zealand white rabbits (approximately 10 weeks old) at four different injection sites. Further immunisations were administered at 28 and 58 days after the initial immunisation as described above with the exception that non-ulcerative Freunds incomplete adjuvant was used. Test bleed samples were taken from the marginal ear vein at 42 and 72 days after the initial immunisation to assess the antibody titre and specificity using an Enzyme Linked Immunosorbent Assay (example 10).

EXAMPLE 10
Enzyme Linked Immunosorbent Assay (ELISA) for Determination of Antibody Titre and Specificity to the 63 kDa PAA-CoA Ligase.
Determination of Antibody Titre A 96 well flat bottomed microtitre plate (Nunc MaxiSorp™) was coated with PAA-CoA Ligase peptide-OVA conjugate (2001 µl/well, 0–10 µg/ml) in phosphate buffered saline pH 7.2 (8 g/l sodium chloride, 0.2 g/l potassium chloride, 1.44 g/l sodium dihydrogen orthophosphate, 0.24 g/l potassium dihydrogen orthophosphate, pH 7.2). The coated microtitre plate was incubated at 4° C. for approximately 18 h after which time the plate was washed four times with wash buffer (10 mM Tris. 0.15M sodium chloride, 0.02% sodium azide, 0.05% Tween 20 pH 7.2) using a Dynatech MRW plate washer. This washing method was used throughout the rest of the procedure unless otherwise stated. Blocking buffer (1.56 g/l sodium dihydrogen orthophosphate. 8.8 g/l sodium chloride, 0.2 g/l ficoll 400, 0.2 g/l polyvinyl-pyrrolidone, 0.5% bovine gamma globulin's from Sigma, pH 7.4, 200 µl/well) was added to the plate and incubated at 37° C. in a Dynatech Varishaker Incubator for 1 h All subsequent incubations at 37° C. were performed using this method. The plate was washed four times and then rabbit polyclonal antibody (100

μl/well, 0–1:500 000 dilution), diluted in assay buffer (50 mM Tris, 150 mM sodium chloride, 1 mM magnesium chloride, 0.5% BSA, 0.25% bovine gamma globulin's, 0.02% sodium azide, pH 7.4), was added to the plate and incubated at 37° C. After washing the plate an anti-rabbit IgG biotinylated antibody from Amersham (100 μl/well, 1:5000 dilution in assay buffer) was added to the plate and incubated at 37° C. The plate was washed and a streptavidin alkaline phosphatase conjugate from Amersham (100 μl/well, 1:2000 dilution in assay buffer) was added to the plate and incubated at 37° C. After washing the plate p-nitrophenyl phosphate (Sigma, 1 mg/ml) dissolved in 0.1 M glycine buffer (7.51 g/l glycine. 203 mg/l magnesium chloride, 136 mg/l zinc chloride, pH10.4) was added to the plate (100μl/well) and incubated at 37° C. for 30 min. Sodium hydroxide (2M, 50 μl/well) was then added to the plate and the absorbance of each well was measured at 405 nm using an Anthos Labtec plate reader. Antibody titres between 1:500000 and 1:1000000 were obtained.

Determination of Antibody Specificity.

To demonstrate that the rabbit polyclonal antibodies would react with the unconjugated PAA-CoA Ligase peptide an ELISA was performed as described above with a modification at the incubation stage which used the rabbit polyclonal antibodies. The antibodies were diluted 1:100 000–1:400 000 in assay buffer and 50 μl of diluted antibody was added to wells containing 50 μl of unconjugated peptide (0–20 μg/ml) prepared in assay buffer containing 2-mercaptoethanol (0.01%, v/v). 50% inhibition of antibody reactivity with the OVA-peptide conjugate was achieved at an unconjugated peptide concentration of approximately 2 μg/ml.

EXAMPLE 11

Determination of Antibody Specificity on Western Blots to PAA-CoA Ligase in Extracts from *Penicillium chrysogenum*, *E. coli* and on purified protein samples.

Extracts prepared from *Penicillium chrysogenum* shake-flask cultures (BW1901 and BW1900A—a strain derived from a random mutation programme), from *E coli* JM109 and samples of purified PAA-CoA ligase protein were Western blotted as described in example 6 except that the membrane was not stained with Coomassie blue. Blotted membranes were placed in blocking buffer (1.56 g/l sodium dihydrogen orthophosphate, 8.8 g/l sodium chloride, 0.2 g/l ficoll 400, 0.2 g/l polyvinyl-pyrrolidone, 0.5% bovine gamma globulin's, pH 7.4) and incubated for approximately 18 h at 4° C. The membrane was then washed four times with wash buffer (10 mM Tris, 0.15M sodium chloride, 0.05% Tween 20, pH7.2) before incubation (room temperature, 60 min) with the rabbit polyclonal antibodies generated as given in example 9 and previously diluted 1:100 in assay buffer (50 mM Tris, 150 mM sodium chloride, 1 mM magnesium chloride, 0.5% BSA, 0.25% bovine gamma globulin's, pH7.4 ). After a further four washes in wash buffer the membrane was incubated with a donkey anti-rabbit IgG horse radish peroxidase conjugate (Bio-Rad, 1:2000 in assay buffer, 60 min, room temperature) followed by a further four washes in wash buffer. The membrane was then incubated with a peroxidase substrate (Bio-Rad Horseradish Peroxidase Conjugate Substrate Kit) for 10 min at room temperature before stopping the reaction by washing the blot in five changes of distilled deionised water. Positive PAA-CoA Ligase protein samples were those with a band at approximately 63 kDa which comigrated with the purified PAA-CoA Ligase band. No positive band at 63 kDa was detected in the *E. coli* JM109 protein extract.

EXAMPLE 12

Construction of a *Penicillium chrysogenum* cDNA bank.

A cDNA bank of *Penicillium chrysogenum* (SmithKline Beecham Strain BW1901) was constructed by following the instruction manual from Stratagene's ZAP Express ™ cDNA Synthesis Kit. RNA was isolated from strain BW1901 as follows. Strain BW1901 grown as given in example 1 for 40 h before harvesting the mycelia by filtration through two Whatman GF/A 9.0 cm glass microfibre filters. The mycelia was washed by 100 ml of DEPC (diethylpyrocarbanate) treated distilled water. The mycelia was then ground in liquid nitrogen using a DEPC treated mortor and pestle. The frozen powdered mycelia was transferred to a 50 ml centrifuge tube containing 10 ml of solution G (4M guanidinium thiocyanate, 50 mM Tris.HCl pH 7.5, 25 mM EDTA). The powder was resuspended in Solution G and left on ice for 15 min. The mycelial debris was pelleted at 17500×g at 4° C. for 20 min. The supernatant was collected into another 50 ml centrifuge tube and the RNA was extracted as Chomczynski and Sacchi (1987) Analytical Biochemistry 162, 156–159. From the total RNA, polyA$^+$ RNA was isolated by using CP Laboratories Mini-Oligo (dT) cellulose spin column kit as per the manufacturer's instructions. The poly$^+$ RNA was analysed by gel electrophoresis as in Sambrook et al (1989) Molecular Cloning, A Laboratory Manual (second edition). Aliquots (5 μg) of polyA$^+$ RNA were taken and used to synthesise double stranded cDNA flanked by EcoRI restriction site at 5' end and a XhoI restriction site at the 3' end of the cDNA, by following Stratagene's ZAP Express™ cDNA synthesis protocol. The cDNA thus synthesised was then size fractionated by passage through Stratgene's Sephacryl S-400 spin columns supplied with the cDNA synthesis kit following the manufacturer's instructions. The size fractionated cDNA was ligated into the XhoI and EcoRI arms of λZAP Express as in Stratagene's Instruction manual. The ligated λDNA was then packaged by using Stratagene's Gigapack II Gold Packaging kit as per the instruction protocol. The resulting cDNA phage were then amplified by plating out, incubating for 8 hours. Over 250,000 independent clones were obtained and the phage eluted in 20 ml of SM medium (0.1M NaCl, 0.01M MgSO$_4$, 0.05M Tris-HCl pH7.5, 0.01% gelatine) per Nunc plate. aliquoted and stored as Sambrook et al. (1989) ibid.

EXAMPLE 13

Immunoscreening of cDNA Bank

The λZAP Express cDNA bank from Example 12 was screened for clones that expressed the 63 kDa PAA-CoA ligase protein using antibodies made as given example 9. The cDNA bank was screened as in Sambrook et al. (1989) ibid. The λZAP Express bank was infected at appropriate dilutions into the *E. coli* strain XL1 Blue MRF'. The infected bacteria were grown for 4 h on Luria agarose containing 10 mM MgSO$_4$, 0.2% maltose and 5 mM IPTG (to induce expression of the cDNA insert) at 37° C. before overlaying with nitrocellulose (Hybond-C super, Amersham) and incubating overnight at 37° C. The filters were then immunoscreened using the primary rabbit antibodies (example 9) at $\frac{1}{1000}$ dilutions, while the secondary antibody, goat anti-rabbit IgG alkaline phosphatase conjugate antibody (Sigma product A-8025) was used at $\frac{1}{2000}$ dilutions. The localisation of positive clones was performed with BCIP/NBT tablets (5 bromo4-chloro-3-indolylphosphate/nitroblue tetrazolium) purchased from Sigma (product B-5655) and used according to the manufacturer's instructions. Twenty four positive clones were identified and cored, resuspended in SM buffer (5.8 g/l NaCl, 2 g/l MgSO$_4$.7H$_2$O, 50 mM Tris-HCl pH7.5, 0.01% gelatine) and rescreened at a lower density of plaques until a positive signal could be identified to a single plaque.

EXAMPLE 14
Subcloning of Positive Clones

The positive λZAP Express cDNA clones identified from the immunoscreen (example 13) were then excised as plasmid pBKCMV derivatives using the ExAssist helper phage and excision protocol provided by Stratagene. The plasmid clones were then be grown up (kanamycin selection) and "mini-prepped" as given in Sambrook et al. (1989) ibid. The plasmids obtained were then analysed by XbaI/SstI double digests in order to characterise the cDNA insert size of the clones. The cDNA insert size ranged from 700 bp to 2.8 kb, with the largest group (12 clones) possessing an insert size of 2.0 kb. The plasmids were also digested with Sau3A (4 base pair cutter) to confirm grouping of clones on the basis of similar restriction patterns. In this way the clones were divided into 6 groups based on common restriction digest patterns. Representative clones from each group were then tested for production of the 63 kDa PAA-CoA ligase protein by Western analysis and also for enzyme activity.

EXAMPLE 15
Demonstration of Positive cDNA Clones Using Western Blotting.

Protein extracts from representative excised immunoscreen positive clones were prepared by taking an overnight culture of the *E. coil* clones grown in Luria broth plus kanamycin (504 g/ml), IPTG (5mM) at 25° C. and adding an equal volume of SDS-PAGE sample buffer followed by boiling and electrophoresis as in example 6. The proteins were then Western blotted to determine the presence of the 63 kDa PAA-CoA ligase protein (example 11). Immunostaining of the membrane was performed as described in example 11 other than that an anti-rabbit IgG alkaline phosphatase conjugate was used (1:2000 dilution in assay buffer) and the phosphatase substrate was BCIP/NBT supplied in tablet form (Sigma) and used according to the manufacturers instructions. One group of clones (cDNA insert size of 2.0 kb) was identified as having a 63 kDa protein (co-migrated with BW1901 control).

EXAMPLE 16
Assay of *E. coli* Clones for Ligase Activity.

Broth containing *E. coli* cells (grown as in example 15) were centrifuged in a refrigerated Denley centrifuge at 4000×g, 4° C. for 7 min to pellet the cells. The supernatant was discarded and the cells resuspended in ligase assay buffer (example 2) at half of the original broth volume. The cells were then chilled on ice before sonicating to disrupt the cells. Conditions for sonication were output 5, 50% duty cycle on an Apollo Electronics Sonicator for 30 s bursts over 7 min on ice. Extracts were either used immediately or stored at −80° C. until used. PAA-CoA ligase activity was demonstrated using the assay procedure described in example 3 except that 40 μl of extract was used and the reaction mixture was incubated for 60 min at 30° C. The presence of PAA-CoA in the assay supernatants was demonstrated using HPLC as described in example 4 with the addition of a Waters 996 photodiode array detector for spectral analysis. PAA-CoA ligase activity was detected in clone 6.6 (representative of the group with a cDNA insert size of 2.0 kb) and the PAA-CoA produced was confirmed by diode array analysis against a PAA-CoA standard.

EXAMPLE 17
Sequence of 5' DNA of PAA-CoA Ligase Clones.

Clone 6.6 (=pPEN09) was "maxi-prepped" and DNA purified by CsCl gradients as in Sambrook et al. (1989) ibid. A restriction map of pPEN09 was prepared by performing single and double enzyme digests (FIG. 2). This clone was then sequenced using the primer (5'-ACAGGAAACAGCTATGACCTTG-3') purchased from Cruachem and using Pharmacia's T7 sequencing kit and following the manufacturer's instructions provided. The sequence of the 5' end of the cDNA insert, shown below, verified that the translated amino acid sequence at the N-terminus of the cDNA matched that of the peptide sequence previously obtained (example 6). except for the starting methionine (absent from the peptide sequence).

```
TCTAAACCCCGAGATCACCTCAGTTTCCTGCACTTTGGAGACCTGCCC           -26

CTATATTACCCCGAGGATTTGGGAAA ATG GTT  TTT TTA CCT            15
                            M   V    F   L   P             5

CCA AAG GAG TCC GGT CAA TTG GAC CCA ATT CC                  48
 P   K   E   S   G   Q   L   D   P   I  P                  16

GAC AAT ATT CCA ATC AGC GAG TTT ATG CTC AAT                 81
 D   N   I   P   I   S   E   F   M   L   N                 27
```

The remainder of pPEN09 was sequenced using standard dideoxynucleotide termination reactions containing 7-deaza dGTP. [$^{35}$S]dATP was used as the label. Sequence reactions were analysed on 6% polyacrylamide wedge gels containing 8M urea [Sanger et al (1977) PNAS 74, 5463–5467; Chen and Seeburg (1985) DNA 4, 165–170]. Nested deletions were generated from both the T7 and T3 ends using ExoII and SI nuclease [Henikoff (1984) Gene 24, 351–359]. The deletion clones were size selected for DNA sequencing by electrophoresis on agarose gels. The selected clones being sequenced as pPEN09. Internal sequencing primers were synthesised as necessary. The complete sequence of the cDNA insert is shown in FIG. 3. The translated protein sequence is shown in FIG. 1.

Comparison of the deduced amino acid sequence of the PAA-CoA ligase protein with the National Biomedical Research Foundation Protein sequence database (NBRF-PIR) and SWISS-PROT Protein Sequence Data Bank (SWISS-PROT) on DNASTAR software gave the best match with 4-coumarate-CoA ligase from potato. Using the DNASTAR megalign programme (clustal method) the PAA-CoA ligase protein and the potato 4-coumarate-CoA ligase were aligned. Analysis of the sequence distances revealed a 25% similarity of amino acids between the two proteins. A similar comparison with acetyl CoA synthetases from fungi (Penicillium, Aspergillus, Neurospora and yeast) showed only a 15% similarity.

The last three amino acids of the PAA-CoA ligase protein are serine-lysine-isoleucine. This amino acid sequence fits the consensus for the C-terminus Microbody Targeting Signal (CMTS) and the same amino acids have been considered essential for targeting the Hansenula polymorpha catalase protein to the microbodies (Didion & Roggenkamp (1992) FEBS Lett. M(2–3), 113–116). The SKI C-terminal tripeptide can also target protein to the microbody in *Neurospora crassa* (de Zoysa & Connerton (1994) Curr. Genet. 26, 430437). The last step of penicillin biosynthesis carried out by the ACTF protein (utilising PAA-CoA—the product of PAA-CoA ligase) has been localised to microbodies in *P. chrysogenum* (Muller et al. (1991) EMBO J. 10(2) 489–495). The ACTF protein also has a CMTS that is required for targeting to the microbody (EP 0488 180 A2). That the PAA-CoA ligase protein has a CMTS is consistent with its role in penicillin biosynthesis.

EXAMPLE 18
Hybridisation of Genomic DNA with PAA-CoA Ligase cDNA Probe

Genomic DNA from a number of strains, including *Penicillium chrysogenum* wild-type NRRL1951, BW1900A, BW1901 was isolated as follows. The strains were grown as in example 1, and harvested after 40 h by filtration through Whatman GF/A glass microfibre filters. The mycelia was rinsed in 0.9M NaCl before freezing in liquid nitrogen. The mycelia was ground to a fine powder in liquid nitrogen and the powder resuspended in solution G (example 12) leaving on ice for 15 min. The mycelial debris was pelleted at 17500×g at 4° C. for 20 min. The supernatant was collected into another 50 ml centrifuge tube and the DNA was extracted with phenol/chloroform pH8.0, extracted with chloroform and ethanol precipitated as in Sambrook et al (1987) ibid. The nucleic acid was resuspended in 10 mM Tris.HCl pH8.0, 1 mM EDTA and the RNA was removed by RNase treatment as in Sambrook et al (1989) ibid. The genomic DNAs were digested with BamHI and the digests were electrophored, blotted onto Hybond N membrane (Amersham) as in Sambrook et al (1989) ibid. The membrane was hybridised with the cDNA insert from pPENO9 as follows: The membrane was pre-hybridised in 6×SSC, 1% SDS, 6% PEG6000, 100 μg/ml denatured, fragmented Herring Sperm DNA at 60° C. for 6h. After this time labelled, denatured cDNA fragment (using Amersham's Megaprime kit and $^{32}$P-dCTP as manufacturer's instructions) was added to the hybridisation solution and the hybridisation continued at 60° C. overnight. The membranes were then washed at 65° C. in 2×SSC, 0.1% SDS for 30 min (twice). Membranes were autoradiographed as Sambrook et al (1989) ibid. Results showed a single common 8 kb BamHI fragment from all the Penicillium strains (including wild-type NRRL 1951) that hybridised to the cDNA probe.

EXAMPLE 19
Construction of λEMBL3 Bank

A shakeflask culture of *P. chrysogenum* SmithKline Beecham strain BW1900A was prepared by inoculating a loopful of spores into 50 ml of ACM media (20 g/l malt extract, 1 gal bacto-peptone, 20 g/l glucose) and incubating with shaking at 25° C. After 40 h growth the mycelia was harvested by filtration through Whatman GF/A glass microfibre filters and rinsed in 0.9M NaCl. The mycelia was then resuspended in 0.9M NaCl containing 10 mg/ml Novozym (Novo Biolabs, Novo Industri. Denmark) and incubated at 25° C. for 2 h. The protoplasts were purified from the mycelial debris by passage through a cotton wool filter before centrifuging at 4000×g for 10 min to pellet the protoplasts. The protoplasts were rinsed twice in 0.9M NaCl before adding 4M guanidinium thiocyanate, 500 mM Tris.HCl pH7.5, 25 mM EDTA to lyse the protoplasts. The debris was removed by centrifugation and the supernatant containing chromosomal DNA, was added to an equal volume of 8M LiCl mixed gently and stored at −20° C. for 30 min. The protein and some RNA was then pelleted by centrifugation (1000×g, 4° C., 10 min) and the supernatant containing chromosomal DNA was ethanol precipitated. The chromosomal DNA was partially digested with Sau3A and the fragmented chromosomal DNA was size fractionated on a sucrose density gradient as in Sambrook et al (1989) ibid. Fractions containing Sau3A fragments greater than 10 kb were pooled and used in the construction of a λEMBL3 bank. The Sau3A genomic fragments were ligated to the λEMBL3 BamHI arms obtained from Promega. The ligated %DNA was then packaged using Promega's Packagene kit. The packaged λDNA was then amplified by infecting *E. coli* strain LE392 cells and the plaques were plated out onto a bacterial lawn and incubating for 8 h at 37° C. as Sambrook et al (1989) ibid. Approximately 18000 independent clones were obtained. The phage were eluted into SM buffer and stored appropriately (as in Sambrook et al., 1989. ibid).

EXAMPLE 20
Cloning the Genomic DNA of PAA-CoA Ligase

From the cDNA clone 6.6 a SstI-XbaI fragment containing the cDNA insert (FIG. 2) was used to probe a λEMBL3 bank (prepared in example 19) by plaque hybridisation as Sambrook et al (1989) ibid (conditions same as in example 18). From the primary screen a number of primary positives were identified and these were picked and used for a secondary screen at lower dilutions. The plaque hybridisation was repeated and individual plaques were identified as hybridising to the PAA-CoA ligase cDNA probe. These λEMBL clones were picked off and amplified. The λEMBL clones were digested with one of BamHI, EcoRI or SalI and all pairwise combinations, along with single digests of genomic DNA from strain BW1900A. The digests were electrophoresed, blotted and characterised by Southern hybridisation and restriction fragments containing the whole PAA-CoA ligase gene were identified. A 6.5 kb EcoRI fragment was taken from some of the λEMBL clones (same size fragments seen in chromosomal DNA digests) and subloned into pIJ2925 (G. R. Janssen and M. J. Bibb (1993) Gene 124 (1) 133–134). A restriction map of the genomic DNA is presented in FIG. 4.

EXAMPLE 21
Transformation of *P. chrysogenum* Strain BW1901 with PAA-CoA Ligase

The 6.5 kb EcoRI subclone in pIJ2925 (example 20, =pAMX131) was used with a linear amdS fragment from p3SR2 (Hynes et al (1983) *Mol. Cell. Biol.* 3, 1430–1439) to co-transform protoplasts of *P. chrysogenum* strain BW1901 (method as Tilburn et al. (1984) Gene 26, 205–221). Transformants were selected for the ability to utilise acetamide. The transformants were then screened for PenV titre. A number of transformants had greater levels of PenV compared to BW1901 control (up to 111% on retests), possibly suggesting the integration of both plasmids. Such a result would support the role of this clone in penicillin biosynthesis.

What is claimed is:

1. An isolated polypeptide having PAA-CoA ligase activity obtainable from *Penicillium chrysogenum* by culturing, harvesting and sonicating the mycelium, removing cell debris and fractionating the sonicate by anion-exchange chromatography, followed by hydrophobic interaction chromatography, affinity chromatography with substrate elution and gel filtration chromatography wherein the active chromatographic fractions are detected using a PAA and coenzyme A-dependent assay.

2. A polypeptide according to claim 1 having an apparent molecular mass of approximately 63 kD by SDS PAGE.

3. A polypeptide according to claim 1 incorporating the sequence of N-terminal amino acids:

V-F-L-P-P-K-E-S-G-Q-L-D-P [SEQ ID NO:3].

4. A polypeptide according to claim 1 which comprises the sequence of amino acids shown in SEQ ID NO:1.

5. A process for preparing an enzyme according to claim 1 which comprises culturing Penicillium sp., followed by extraction and purification wherein the active fractions are detected using a PAA and Co-enzyme A dependent assay.

6. An isolated polypeptide having PAA-CoA ligase activity obtainable from Penicillium chrysogenum incorporating the sequence of N-terminal amino acids:

V-F-L-P-P-K-E-S-G-Q-L-D-P [SEQ ID NO:3].

7. An isolated polypeptide having PAA-CoA ligase activity obtainable from *Penicillium chrysogenum* which comprises the sequence of amino acids shown in SEQ ID NO:1.

8. An isolated DNA encoding a polypeptide having PAA-CoA ligase activity obtainable from *Penicillium chrysogenum* by culturing, harvesting and sonicating the mycelium, removing cell debris and fractionating the sonicate by anion-exchange chromatography, followed by hydrophobic interaction chromatography, affinity chromatography with substrate elution and gel filtration chromatography wherein the active chromatographic fractions are detected using a PAA and coenzyme A-dependent assay.

9. The DNA according to claim 5 having the configuration of restriction sites as shown in FIG. 2 or 4.

10. The DNA according to claim 9 which comprises the DNA sequence in SEQ ID NO:2.

11. An isolated DNA, and fragments thereof, encoding a polypeptide having PAA-CoA ligase activity which hybridises under conditions of high stringency with the DNA according to claim 8 as follows: prehybridized at 60° C. 6×SSC, hybridized overnight at 60° C. and washed at 65° C. in 2×SSC.

12. A vector comprising DNA according to any one of claims 8–11 for expressing an enzyme having PAA-CoA ligase activity in a suitable host organism.

13. A host transformed with the vector of claim 12.

14. A process for producing penicillin comprising, culturing the transformed host according to claim 13 and recovering penicillin from the culture.

15. An isolated DNA encoding a polypeptide having PAA-CoA ligase activity obtainable from *Penicillium chrysogenum* which incorporates the sequence of N-terminal amino acids:

V-F-L-P-P-K-E-S-G-Q-L-D-P [SEQ ID NO:3].

16. An isolated DNA encoding a polypeptide having PAA-CoA ligase activity obtainable from *Penicillium chrysogenum* which comprises the sequence of amino acids shown in SEQ ID NO:1.

* * * * *